US00PP14344P29

(12) United States Plant Patent
Diboll

(10) Patent No.: US PP14,344 P2
(45) Date of Patent: Dec. 2, 2003

(54) SPOROBOLUS PLANT NAMED 'MORNING MIST'

(50) Latin Name: *Sporobolus heterolepis*
Varietal Denomination: Morning Mist

(76) Inventor: Neil Hart Diboll, P.O. Box 306, Westfield, WI (US) 53964-0306

( * ) Notice: Subject to any disclaimer, the term of this patent is extended or adjusted under 35 U.S.C. 154(b) by 0 days.

(21) Appl. No.: 10/319,261

(22) Filed: Dec. 13, 2002

(51) Int. Cl.[7] ..... A01H 5/00
(52) U.S. Cl. ..... Plt./384
(58) Field of Search ..... Plt./384

*Primary Examiner*—Bruce R. Campell
*Assistant Examiner*—Annette H. Para
(74) *Attorney, Agent, or Firm*—Penny J. Aguirre

(57) ABSTRACT

A new cultivar of *Sporobolus heterolepis* 'Morning Mist'. 'Morning Mist' is characterized by an unusually high number of sturdy, red fruiting culms borne at a consistent height above dense gently arching foliage.

2 Drawing Sheets

BACKGROUND OF THE INVENTION

The present invention relates to a new and distinct cultivar of *Sporobolus heterolepis* and will be referred to hereafter by its cultivar name, 'Morning Mist'. 'Morning Mist' represents a new cultivar of Prairie Dropseed, an ornamental grass grown for landscape use.

The inventor discovered and selected the new cultivar, 'Morning Mist', in a cultivated field in Westfield, Wis. in the fall of 1991. 'Morning Mist' was discovered as a naturally occurring variant seedling in a cultivated field sown for commercial seed production. The seeds sown were produced by open-pollination of unidentified selections of *Sporobolus heterolepis,* therefore, 'Morning Mist' has no identifiable parents.

The new cultivar 'Morning Mist' is unique in several characteristics, which in combination make this new invention unlike any other known cultivars of *Sporobolus heterolepis* known to the inventor. 'Morning Mist' has an abundance of blooms held on sturdy red culms and rachis with foliage that is upright but gently arching. The species typically has fewer fruiting culms, with great variability in inflorescence height and culms that are effectively brown and tend to lodge after seed maturation.

Asexual reproduction of the new cultivar was first accomplished by root division in Westfield, Wis. in 1993 by the inventor. The characteristics of this cultivar have been determined to be stable and are reproduced true to type in successive generations.

SUMMARY OF THE INVENTION

The following traits have been repeatedly observed and represent the characteristics of the new cultivar. 'Morning Mist' has not been observed under all possible environmental conditions. The phenotype may vary somewhat with variations in temperature, daylength, light intensity, soil types, and water and fertility levels without, however, any variance in genotype. The measurements, observations, and descriptions that follow describe plants grown outdoors in Westfield, Wis. These attributes in combination distinguish 'Morning Mist' from any known selections of *Sporobolus heterolepis.*

1. The plant habit of 'Morning Mist' is upright and slightly arching. The habit of the species is typically a mound that cascades to the ground from the center.
2. The flower panicles of 'Morning Mist' are held at a more consistent height than is typical of the species. Flowering stem height for 'Morning Mist' ranges from 60 to 90 cm whereas it is typical of the species to have flower stems on the same plant ranging in height from 50 to 130 cm.
3. The flower panicles are held on sturdy culms and do not droop as the seed matures. It is typical for the flowering culms of the species to lodge towards the ground as the seeds ripen.
4. The culms and rachis of 'Morning Mist' are consistently a deep red. The species typically has hints of this coloration but it is inconsistent, not as deep in color, and the general appearance of the culms is a light brown color.
5. 'Morning Mist' has significantly more fruiting culms than is typical of the species. A 3 year-old clump produces approximately 100 fruiting culms. The species typically has 40 to 50 fruiting culms arising from a clump of similar age and size.
6. The foliage color of 'Morning Mist' is typical of the species: deep green in summer and turning a golden orange in fall.
7. 'Morning Mist' is tolerant to a wide range of soil growing conditions; growing well in full sun to light shade in any well-drained soil. It is tolerant of alkaline soils and drought when established.

BRIEF DESCRIPTION OF THE DRAWING

The photographs used in these drawings were taken of a 3 year old plant grown from a single root division of 'Morning Mist' and grown outdoors in a trial bed in Westfield, Wis.

Figure One was taken in October, and shows the habit of the entire plant and the characteristics of the fruiting culms.

Figure Two was taken in June and the summer foliage color is depicted. The colors in the photographs are as close as possible with conventional photography.

BOTANICAL DESCRIPTION OF THE PLANT

The following is a detailed description of the new cultivar as grown in an outdoor trial bed for three years from a single root division in Westfield, Wis. The color determination is in accordance with The 1995 R.H.S. Colour Chart of The Royal Horticultural Society, London, England, except where general color terms of ordinary dictionary significance are used.

Botanical classification: 'Morning Mist' is a cultivar of *Sporobolus heterolepis.*

Commercial classification: Prairie dropseed.

Parentage: Naturally-occurring seedling selection from an open pollinated crossing of unidentified selections of *Sporobolus heterolepis.*

General description:

*Blooming period.*—August through September with seeds forming in October.

*Plant habit.*—Herbaceous perennial grass, upright with arching clumps of dense, fine-textured foliage, long-lived.

*Height and spread.*—60 to 90 cm in height in bloom and 66 to 75 cm in width to the tips of the arching foliage after three years from a 6 cm division. Height of the foliage averages about 45 cm. Moderate vigor.

*Hardiness.*—Zone 3 to 9.

*Culture.*—Grows well in full sun to light shade, in any well-drained soil. Tolerant of drought and alkaline soils.

*Diseases and pests.*—*Sporobolus heterolepis* is relatively disease free. No susceptibility or resistance to diseases or pests has been observed for 'Morning Mist'.

*Root description.*—Fibrous, wiry, dark brown, formed on short, tightly packed, tightly packed non-creeping rhizomes, 2 cm in length and up to 1 cm in width, deep rooted.

Growth and propagation:

*Propagation.*—Root division and tissue culture.

*Time required for root development from a single division.*—10 to 12 weeks to fully develop in a one-gallon container in a greenhouse with ambient lighting and an average temperature of 68° F.

Culm (stem) description:

*General.*—Cylindrical, pithy, sturdy, erect.

*Culm color.*—178A, stem is covered by leaf sheath prior to last leaf node.

*Culm size.*—1.0 to 1.5 mm in diameter, averaging 75 cm in height from base to tip of flower panicle.

*Stem surface.*—Glabrous.

*Internode length.*—16 to 18 cm.

*Ligule.*—Very fine white hairs, 2 mm in length.

Foliage description:

*Leaf shape.*—Linear, flat to involute as they dry.

*Leaf division.*—Simple.

*Leaf base.*—Sheathed to base of culm.

*Leaf apex.*—Attenuate.

*Leaf venation.*—Parallel, only the midrib is distinct and recessed on the upper surface, slightly darker in color on summer leaves on upper surface only.

*Leaf margins.*—Entire.

*Leaf attachment.*—Sheathed. About one half to three fourth of the total length of the leaf is sheathed from the base of culm, with the upper portion extended out from the culm. Sheath surrounds the culm with overlapping margins.

*Leaf size.*—Width; 3 mm at base to 0.5 mm at apex, average of 1.75 mm. Length; 42 to 60 cm.

*Leaf number.*—Typically 3, less commonly 2 or 4.

*Leaf surface.*—Summer foliage; nitid on upper surface, glabrous on lower surface. Fall foliage is glabrous on upper and lower surfaces.

*Leaf color.*—Summer: upper and lower blades; 137A, sheaths 137B. Fall: upper and lower surface 22A. Winter 20C.

Flower description:

*Type.*—Open panicle, composed of pedicelled spikelets, 1 floret per spikelet.

*Lastingness of inflorescence.*—Panicles are persistent, lasting from mid August until seed drop in late October, actual floral parts are insignificant and minuscule.

*Fragrance.*—Pungent, popcorn-like.

*Floret bud.*—4 to 5 mm in length and 1.5–2 mm in width prior to opening in July. Color 137C tinged with 177A. Flower is enclosed by an outer membranaceous bract (lemma), a thin inner bract (palea) and two glumes. The first glume is 2 to 4 mm in length, the second glume is 4 to 5 mm in length.

*Panicle size.*—15 to 17 cm in height and 6 to 8 cm in width.

*Pedicels.*—2 to 6 mm in length, color 178A.

*Rachis.*—40 to 50 cm from last leaf node to tip of panicle, 0.25 to 1 mm in width.

*Panicle color.*—Seed heads 155A, effect is white on red rachis.

Reproductive organs: Anthers 3 (pollen not visible), Stigmas 2, ovary is one-locular and superior; organs are minute and inconspicuous.

*Caryopsis.*—1.5 mm in diameter, globose, shiny, color is 146C turning towards 202A as it matures. Readily drop when mature.

I claim:

1. A new and distinct cultivar of Sporobolus plant named 'Morning Mist' substantially as herein illustrated and described.

* * * * *

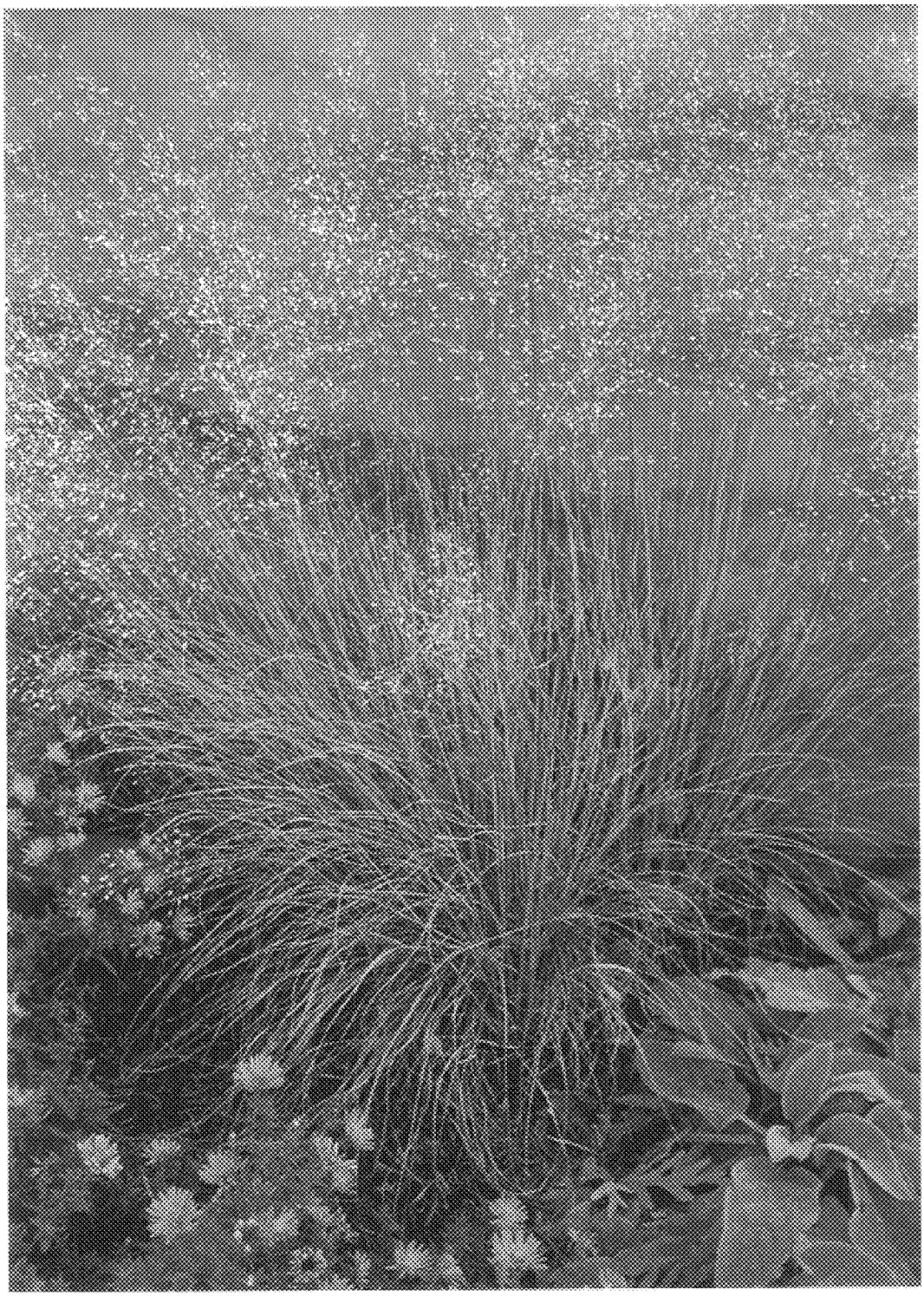
Figure One

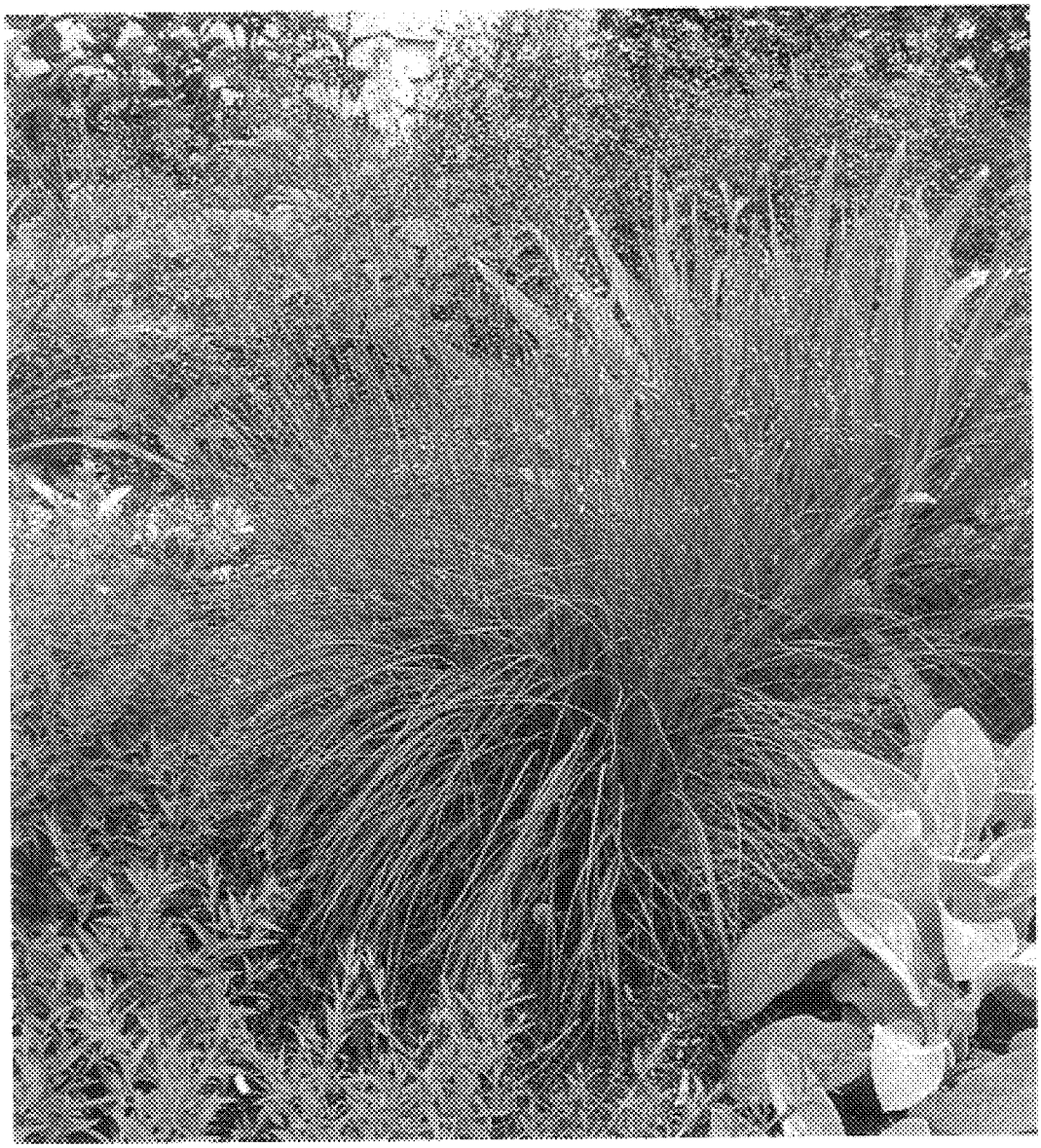
Figure Two